(12) United States Patent
Holztrattner et al.

(10) Patent No.: US 11,393,314 B2
(45) Date of Patent: Jul. 19, 2022

(54) ELECTRICAL INSTALLATION HAVING AN EMERGENCY SIGNAL INPUT FOR RECEIVING AN EMERGENCY SIGNAL TRANSMITTED BY RADIO

(71) Applicant: Adaptive Regelsysteme Gesellschaft M.B.H., Salzburg (AT)

(72) Inventors: Dietmar Holztrattner, Golling (AT); Ulrich Klapper, Rankweil (AT); Wernich de Villiers, Dornbirn (AT)

(73) Assignee: Adaptive Regelsysteme Gesellschaft M.B.H., Salzburg (AT)

( * ) Notice: Subject to any disclaimer, the term of this patent is extended or adjusted under 35 U.S.C. 154(b) by 0 days.

(21) Appl. No.: 17/254,730

(22) PCT Filed: Jun. 19, 2019

(86) PCT No.: PCT/EP2019/066125
§ 371 (c)(1),
(2) Date: Dec. 21, 2020

(87) PCT Pub. No.: WO2019/243387
PCT Pub. Date: Dec. 26, 2019

(65) Prior Publication Data
US 2021/0272435 A1 Sep. 2, 2021

(30) Foreign Application Priority Data

Jun. 21, 2018 (AT) .............................. A 50516/2018

(51) Int. Cl.
*G08B 21/00* (2006.01)
*G08B 21/02* (2006.01)
(Continued)

(52) U.S. Cl.
CPC ............ *G08B 21/02* (2013.01); *G08B 21/182* (2013.01); *G08B 25/10* (2013.01); *H02H 1/0007* (2013.01)

(58) Field of Classification Search
CPC ...... G08B 21/02; G08B 21/182; G08B 25/10; G08B 21/185; H02H 1/0007; H02H 5/12;
(Continued)

(56) References Cited

U.S. PATENT DOCUMENTS 3,328,697 A 6/1967 Duncan et al.
3,784,842 A * 1/1974 Kremer ................. H02H 3/162
307/326

(Continued)

FOREIGN PATENT DOCUMENTS

CA 2617976 A 7/2009
DE 3903025 A1 8/1990
(Continued)

*Primary Examiner* — Anh V La
(74) *Attorney, Agent, or Firm* — Dykema Gossett PLLC

(57) ABSTRACT

Various aspects of the present disclosure are directed to a system for increasing the protection against electric shocks of a person working in proximity to an electrical system. In one example embodiment, the system includes a plurality of first radio terminals, via each of which a radio link for receiving an emergency signal can be established. The system further including a protective device to be worn by the person and for detecting an electrical body current. The protective device including a second radio terminal that, in the event that an unacceptable body current is detected, outputs and transmits an emergency signal via a radio link established between one of the first plurality of radio terminals and the second radio terminal.

25 Claims, 4 Drawing Sheets

(51) Int. Cl.
*G08B 21/18* (2006.01)
*G08B 25/10* (2006.01)
*H02H 1/00* (2006.01)

(58) Field of Classification Search
CPC ......... H02H 3/16; A61B 5/1112; A61B 5/746; A61B 2562/0219; A61B 5/1113; A61B 5/11; A61B 5/0816; A61B 5/318; A61B 5/6804; A41D 1/002; A41D 31/26; A41D 13/008; G01R 19/15
USPC .......................... 340/664, 657, 662, 660, 653
See application file for complete search history.

(56) References Cited

U.S. PATENT DOCUMENTS

| | | | |
|---|---|---|---|
| 6,011,471 A * | 1/2000 | Huang | G08B 13/1418 340/539.1 |
| 9,508,237 B1 | 11/2016 | Mercado et al. | |
| 9,698,590 B1 * | 7/2017 | Mercado | H02H 5/12 |
| 10,247,763 B1 * | 4/2019 | Wu | A41D 19/01594 |
| 2004/0197608 A1 | 10/2004 | Fuglevand | |
| 2007/0229298 A1 | 10/2007 | Frederick | |
| 2016/0235374 A1 * | 8/2016 | Miller | G06F 1/163 |
| 2017/0263097 A1 * | 9/2017 | Song | G06Q 50/10 |

FOREIGN PATENT DOCUMENTS

| | | |
|---|---|---|
| DE | 4219894 A1 | 12/1993 |
| DE | 4438063 A1 | 5/1995 |
| JP | 2009020847 A | 1/2009 |

\* cited by examiner

ELECTRICAL INSTALLATION HAVING AN EMERGENCY SIGNAL INPUT FOR RECEIVING AN EMERGENCY SIGNAL TRANSMITTED BY RADIO

CROSS-REFERENCE TO RELATED APPLICATIONS

This application is a national stage filing based upon International PCT Application No. PCT/EP2019/066125, filed 19 Jun. 2019, which claims the benefit of priority to Austria application No. A 50516/2018, filed 21 Jun. 2018.

BACKGROUND

The present invention relates to an electrical system having an emergency signal input for receiving an external emergency signal sent via a radio link, wherein a predetermined action is triggered in the electrical system when the emergency signal is received. The invention also relates to an arrangement and a method to perform work on the electrical system by a person.

It is common in electrical systems, especially in an industrial environment, to provide an emergency stop in order to switch off a conducting or live component that is part of the emergency stop circuit if a person touches the same. With such safety devices, the protection against electric shock due to an unintentional contact of people working on conducting parts or live parts can be increased by other people present triggering the emergency stop in the event of a fault. However, this requires that at least one further person is in the vicinity of an electrical accident and has knowledge of the electrical accident, which is not always the case.

Other common safety devices in electrical systems are circuit breakers for switching off circuits in the event of an unacceptable electrical current and ground-fault circuit interrupters that are intended to respond in the event of unacceptable earth fault currents. However, these can only provide protection if they actually trip in the event of an error. Due to possible high operating currents or slow reaction times, there may be a danger for people working on the electrical system despite such safety devices.

Methods and devices for a better protection of persons against unacceptable electrical body currents are therefore already known. DE 39 03 025 A1, for example, describes such a method and such a device, wherein an electrode connected to a control device is arranged on at least two extremities of the person, for example on the arms or legs. Via the electrodes, the control device detects a body current caused by a contact with an external electrical potential. If such a current flow is detected, the control device activates a shutdown device with which the further supply of current to the contact point is interrupted. The electrodes and the control device can be arranged on an item of clothing with a wireless connection between the control device and the switch-off device. DE 44 38 063 A1 describes a similar protective device. Such protective devices can increase the safety of persons working on conducting parts or live parts against electric shock due to unintentional contact.

In the case of a wireless connection between the control unit and the disconnection device, the function of the protective device also depends on whether there is a radio channel for the data transmission. This can be problematic in large electrical systems or in buildings if it is not noticed that the radio channel between the control unit and the disconnection device is interrupted, for example if the person is in a radio shadow, or if the radio channel is impaired, for example by electromagnetic interference fields in the vicinity of electrical systems.

It is therefore the object of the present invention to increase the safety of persons in the area of an electrical system against electric shock when touching conducting or live parts of the electrical system.

SUMMARY OF THE INVENTION

According to the invention, this object is achieved in that a plurality of first radio terminals are provided on the electrical system, via each of which a radio link for receiving the emergency signal can be established. This way, even in large or distributed electrical systems, the probability can be increased that at least one radio link can be established to receive an emergency signal. A disruption of the radio link for transmitting the emergency signal, in particular one that is unnoticed, can thus be largely avoided.

A person working on the electrical system preferably wears a protective device for detecting an electrical body current, with a second radio terminal being provided on the protective device and, in the event of an unacceptable body current being detected, the protective device outputs and transmits an emergency signal to the emergency signal input via a radio link generated between one of the first radio terminals and the second radio terminal. As soon as the protective device detects an unacceptable body current (which can be configured accordingly), an emergency signal is triggered, which then triggers the preset action. In this way, the protection of the person is no longer tied to the presence of another person or on the activation of other safety devices.

Further advantageous embodiments and effects of the invention can be gathered from the dependent claims and the following description.

BRIEF DESCRIPTION OF THE DRAWINGS

In the following, the present invention is described in greater detail with reference to FIGS. 1 to 8, which, by way of example, show schematic and non-limiting advantageous embodiments of the invention. In the drawings.

DETAILED DESCRIPTION

Figure 1:
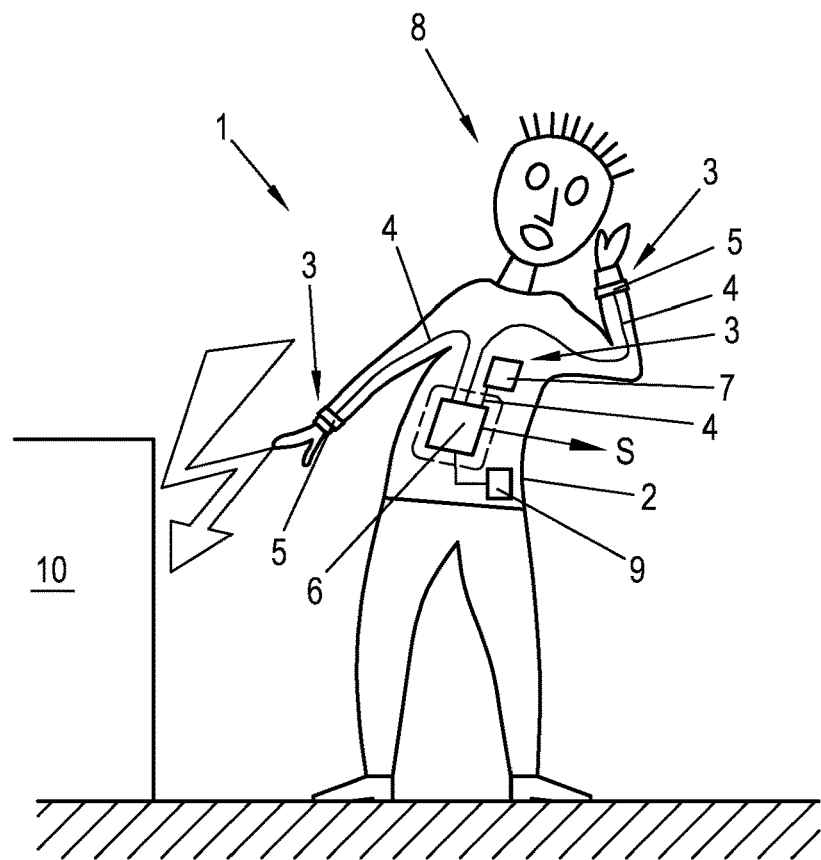
FIG. 1 shows a protective device used for to the invention.

The present invention uses a protective device 1, the basic function of which is known from prior art and which is explained in more detail with reference to FIG. 1 for a better understanding. The protective device 1, or at least parts thereof, is arranged on or integrated in an item of clothing 2, in this case a shirt. Of course, other items of clothing 2, for example trousers, a sweater, a T-shirt, a jacket, overalls, etc., can also be used. Even combinations of several items of clothing 2 are also possible, for example a combination of trousers and shirt, etc. At least one sensor 3 is arranged on the item of clothing 2 in order to detect an electrical body current flowing through the human body. Electrodes 5 can, for example, be used as a sensor 3 in order to detect an electrical potential or an electrical current. The electrodes 5 are preferably arranged at exposed locations on the item of clothing 2, for example in the region of the extremities, i.e., for example on sleeves, trouser legs or hoods. A biometric sensor 7 can also be used as a sensor 3 in order to detect a biometric signal, for example the heart rate, the amplitude or the course of the heartbeat, the respiratory rate, the skin resistance, etc. By evaluating the biometric signal, in particular the heartbeat (frequency, amplitude and/or course), conclusions can also be drawn about a flowing electrical body current.

For this purpose, the sensor 3, or the sensors, can preferably be integrated in the item of clothing 2 but can also be applied separately, for example by means of a cuff, bracelet or belt. In a possible embodiment, a sensor 3 could be designed as an electrode 5 in the form of a known Rogowski coil (as in FIG. 1) in order to detect an electrical current flowing through an extremity or another part of the human body. For this purpose, the electrode 5 can be placed in a ring around an extremity, for example in a waistband of a sleeve or a trouser leg of the item of clothing 2. In order to detect an electrical potential, the electrode 5 must be in contact with the skin in an electrically conductive manner, whereas this would not be absolutely necessary in the case of a Rogowski coil, for example. In order to detect the heartbeat, a corresponding biometric sensor 7, for example a heart rate sensor, could be integrated in the item of clothing 2 in the region of the chest, or a corresponding chest strap could be applied.

A sensor 3 is connected via at least one signal line 4 to an evaluation unit 6 (for example, in the form of a computing unit, possibly also with corresponding software). The signals detected by the at least one sensor 3 are evaluated in the evaluation unit 6. An electrical potential detected with an electrode 5 as the sensor 3 or a detected flowing electric current can be evaluated, for example. An applied electrical voltage can be determined between two detected electrical potentials, for example with two sensors 3 designed as electrodes 5, and evaluated in the evaluation unit 6. A resistance measurement can also be carried out regularly or continuously between two electrodes 5 in order to check whether the item of clothing 2 is properly connected to the body of the person 8. The evaluation of the body current or of a potential difference can likewise be carried out with suitable hardware or digitally, which requires an A/D conversion and the corresponding hardware and software. In the event that a dangerous body current is detected, for example when an abnormal heartbeat, a dangerous current flow or a dangerous potential difference (voltage) between two electrodes 5 is detected, which in turn indicates a current flow through the body, the evaluation unit 6 generates an emergency signal S which can be used to trigger a desired action. For this purpose, corresponding limit values for an acceptable body current, for example an acceptable potential difference or an acceptable current, can of course also be stored or specified in the evaluation unit 6, which can also be adjustable. Likewise, patterns of a biometric signal that indicate a dangerous body current can also be stored in the evaluation unit 6.

Advantageously, different sensors 3 can be provided on the item of clothing 2 in order to increase the reliability of the detection of dangerous electrical body currents. For example, electrodes 5 could be provided on extremities and additionally a biometric sensor 7 for detecting the heartbeat, as shown in FIG. 1.

The safety of the protective device 1 can also be increased by providing redundancies. For example, more than one signal line 4 can be provided per sensor 3 so that possible cable breaks or contact errors do not have to lead to a failure of the safety function, or a cable break or contact error can even be recognized and possibly also indicated.

The evaluation unit 6 is preferably held or carried by the person 8 who wears the protective device 1. This evaluation unit could be arranged, for example, in a shoulder bag or a backpack, but could also be pouched into a pocket of the item of clothing 2 or could also advantageously be integrated, wholly or partially, in the item of clothing 2, for example in the form of an intelligent item of clothing with integrated electronics.

The protective device 1 thus consists, for example, of an item of clothing 2 with at least one sensor 3 and an evaluation unit 6 which is connected to the at least one sensor 3 by at least one signal line 4 and which evaluates a signal detected by the sensor 3 in order to detect a dangerous electrical body current. The emergency signal S of the evaluation unit 6, or generally of the protective device 1, can be used by the electrical system 10 or parts thereof to set certain configured actions in order to increase the protection of a person 8 against electric shock. Preferably, switching actions are configured in order to disconnect the electrical system 10 or parts thereof from voltage.

Figure 2:
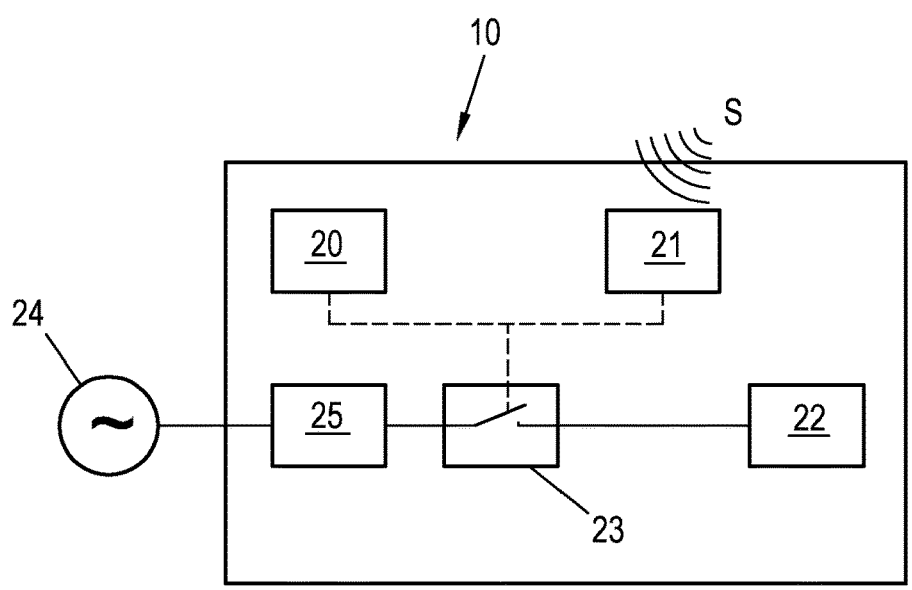
FIG. 2 shows the integration of an emergency signal input for receiving an emergency signal in an electrical system.

This is explained by way of example with reference to FIG. 2, which shows a device 11 as an example of an electrical system 10 or part of an electrical system 10. A current and/or voltage generator 25 is provided in the device 11, which generates the required electrical currents and/or voltages at the current and voltage outputs 22 of the device 11. For this purpose, the device 11 is connected to a power supply 24, which can be external (for example, a power grid or an external battery) or also internal (for example, in the case of a battery-operated device). In the device 11, a disconnection unit 23 is provided between the current and/or voltage generator 25 and the current and voltage outputs 22. The disconnection unit 23 could, however, also be provided upstream from the current and/or voltage generator 25 or at another suitable point in the device 11. The disconnection unit 23 can, of course, also have a multi-pole design, depending on the number of current and voltage outputs 22. The emergency stop switch 20, when actuated, activates the disconnection unit 23, for example a disconnection relay, in the device 11, which switches off and/or short-circuits the current and voltage outputs 22 of the device 11. An emergency signal input 21 is additionally provided on the electrical system 10, which, when an emergency signal S is received, in particular from the protective device 1, actuates the disconnection unit 23 of the emergency stop circuit. According to the invention, the emergency signal input 21 is consequently also connected to the disconnection unit 23 and activates the disconnection unit 23 when an emergency signal S is received via the emergency signal input 21. However, several serially connected disconnection units 23, each of which is controlled separately, could also, of course, be provided in the device 11 with the same effect, for example a disconnection unit for the emergency stop switch 20 and a disconnection unit 23 for the emergency signal input 21. The emergency signal input 21 does not necessarily have to be integrated into the electrical system 10, but could also be designed as a separate unit that is connected to the electrical system 10 in a suitable manner.

Other examples of an electrical system 10 are an electrical energy distribution network in a building or an electrical energy supply in a production system, in which an emergency stop circuit does not necessarily have to be provided, but in which an emergency signal input 21 is provided for receiving an emergency signal S to make it possible to trigger a configured (switching) action in the electrical system 10.

The electrical system 10, or a part thereof, can also, of course, be switched off in other ways. A switch could be activated, for example. Likewise, a circuit could be short-circuited (for example, by connecting a phase to the neutral conductor) in order to trigger a circuit breaker to disconnect the circuit from the network. A sufficiently high ground fault current could also be generated (for example, by connecting a phase to the ground with a resistor) to trip a ground-fault circuit interrupter. There are, of course, also other options for switching off the electrical system 10 or parts thereof.

The invention assumes that the emergency signal S is emitted wirelessly and received wirelessly at the emergency signal input 21. For this purpose, a suitable radio link can be provided between the protective device 1 and the emergency signal input 21, for which existing standards can also be used. This naturally means that a first radio terminal 90 is provided on the emergency signal input 21 and a second radio terminal 91 is provided on the protective device 1, between which the radio link is established. The radio link can also be bidirectional.

The second radio terminal 91 of the protective device 1 is preferably arranged on the item of clothing 2 or integrated into the item of clothing 2 (e.g., again in the form of intelligent clothing with integrated electronics) and connected to the evaluation unit 6 or another control unit in the protective device 1.

In certain applications, for example in buildings or on large electrical systems, the radio link between the protective device 1 and the emergency signal input 21 can be interrupted easily and without noticing, in particular when the person 8 wearing the protective device 1 is moving. This can lead to false activations of the protective device 1 if a missing radio signal in the emergency signal input 21 triggers a switching action. In the worst case, the protective device 1 no longer provides protection for the person 8 carrying said device with this circumstance going unnoticed.

The electrical system 10 could also be configured differently depending on how dangerous the application is so that an interruption of the radio link forces a switch-off if the application is very dangerous but does not do so if the application is less dangerous.

Figure 3:
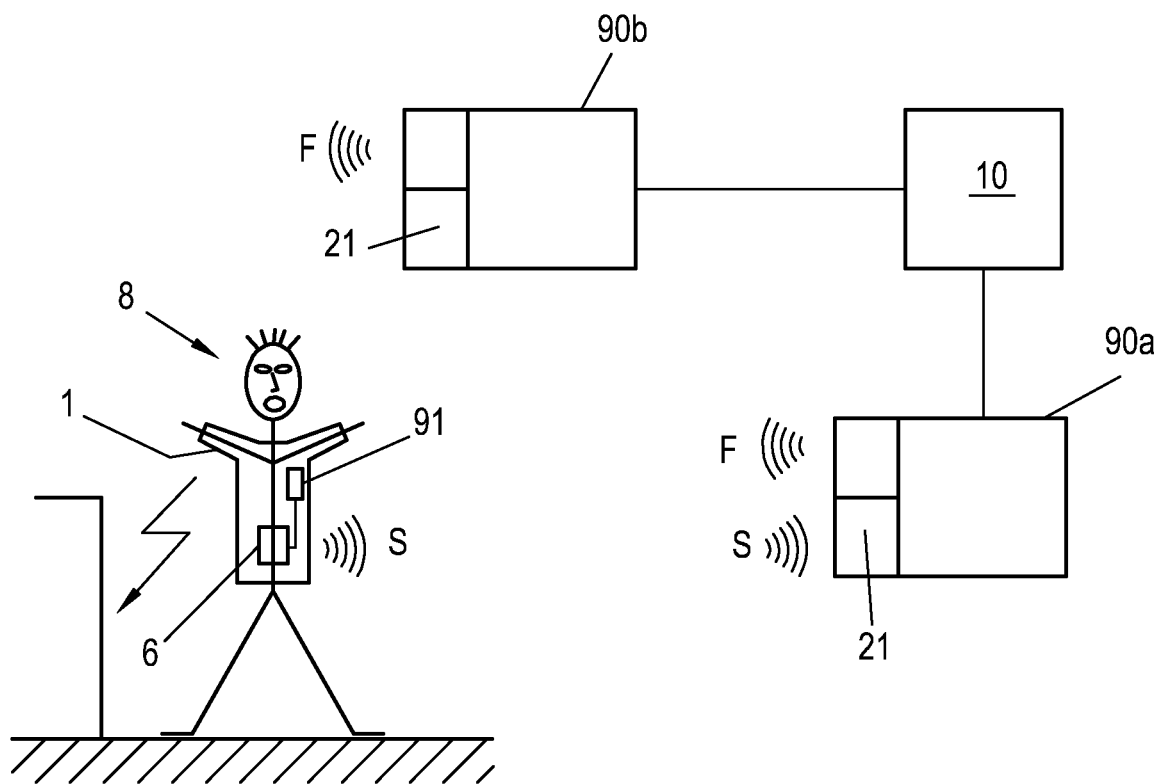
FIG. 3 shows a system with a plurality of radio receivers for transmitting the emergency signal from the protective device to an electrical system.
Figure 4:
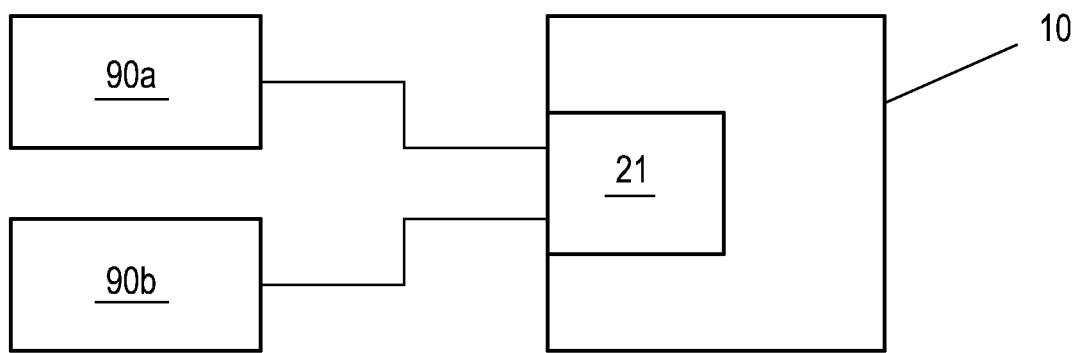
FIG. 4 shows an electrical system with an emergency signal input with which a plurality of radio receivers are connected.

In order to prevent an unnoticed interruption of the radio link, it is provided according to the invention that a plurality of first radio terminals 90a, 90b are spatially distributed in the region of the electrical system 10, as shown in FIG. 3. An emergency signal input 21 can be integrated in a first radio terminal 90a, 90b such that a first radio terminal 90a, 90b with the emergency signal input 21 triggers the intended action in the electrical system 10, as shown in FIG. 3. The emergency signal input 21 can also be implemented in the electrical system 10 and connected to the plurality of first radio terminals 90a, 90b, as shown in FIG. 4. Mixed forms are conceivable as well.

The second radio terminal 91 of the protective device 1 can establish a radio link to each first radio terminal 90a, 90b.

In a simple embodiment of the invention, all the first radio terminals 90a, 90b use the same radio channel for the radio link. If the first radio terminals 90a, 90b are arranged sufficiently close, it can be assumed that there is always at least one radio link between a first radio terminal 90a, 90b and the second radio terminal 91 on the protective device 1, via which an emergency signal S can be transmitted. The arrangement of the first radio terminals 90a, 90b on the electrical system 10 can of course be planned accordingly.

In an improved embodiment, the radio link is a multi-channel link with at least enough channels that a radio link can always be established via a clearly identifiable radio channel. This means that different radio channels do not necessarily have to be assigned for all first radio terminals 90a, 90b, but rather the same radio channels can also be used in different first radio terminals 90a, 90b, provided the radio channels do not overlap. However, each first radio terminal 90a, 90b can of course also have its own radio channel assigned. Any multichannel radio links can be used here, for example on the basis of frequency division multiplex or time division multiplex. An example of a suitable radio link is a Long Range Network (LoRa).

The protective device 1 can be in bidirectional radio communication with the first radio terminals 90a, 90b in the reception area in order to be able to receive a radio signal F that was sent by the first radio terminals 90a, 90b in the protective device 1. The radio signal F from a first radio terminal 90a, 90b is transmitted continuously or at least at regular intervals and is received by the second radio terminal 91 of the protective device 1.

The signal quality of a radio channel between the protective device 1 and a first radio terminal 90a, 90b can thus be evaluated. The protective device 1 can, for example, receive radio signals F from the first radio terminals 90a, 90b in the reception area on different radio channels and evaluate the signal level of the radio signal F or another suitable property of the radio signal F. The protective device 1 can then decide via which radio channel an emergency signal S should be sent, if necessary. However, it can also be provided that the protective device 1 sends out a signal at regular intervals that is received by the first radio terminals 90a, 90b in the reception area and is used to assess the signal quality of the radio channels. In this way, the protective device 1, for example from a first radio terminal 90a, 90b, can be informed via a radio signal F about the radio channel via which an emergency signal S should be transmitted.

This way, the person 8 who wears the protective device 1 can move through the building or in an electrical system without losing the radio link. The radio link may move along accordingly by assigning the best first radio terminal 90a, 90b or best radio channel (in the sense of the best or at least sufficient signal quality of the radio channel) for a radio link that may be necessary between the protective device 1 and the emergency signal input 21.

For the invention, however, it is in principle unimportant where the decision which first radio terminal 90a, 90b is used for the communication is made. The decision could be made in the protective device 1, in the second radio terminal 91, in the first radio terminals 90a, 90b, in the emergency signal input 21 or also in the electrical system 10.

In the protective device 1, preferably on the item of clothing 2 or on an external unit that is in data connection with the protective device 1, at least one further sensor 9 can optionally be provided for detecting a further variable (FIG.

1), which detects a further condition of the person 8 (in addition to a possible body current). The further sensor 9 can, for example, be an acceleration sensor in order to be able to determine a fall of the person 8. A position sensor as a further sensor 9 can be used to detect if the person 8 is lying down. The further sensor 9 can be designed to record an ECG (electrocardiogram) which, in connection with an electrical accident, can provide important information about the condition of the person 8 having the accident. The respiration of the person victim 8 having the accident can also be recorded by means of an acceleration sensor or movement sensor as a further sensor 9. Of course, several further sensors 9 can also be provided on the protective device 1 with any combinations of the above sensors 9 being conceivable.

Values acquired with the sensor 3, or the sensors 3, and/or values acquired with at least one further sensor 9 can also be stored in the protective device 1 in a memory unit, for example in evaluation unit 6. This makes it possible to read stored values at a later point in time or to transmit them to other locations.

In many situations, the protective device 1 can successfully actuate a preset (switching) action via an emergency signal input 21 and thus switch the electrical system 10 or at least parts of it into a currentless and voltage-free state. When the protective device 1 is activated, however, an electric shock has already occurred in these situations. The affected person 8 can, however, sometimes work in remote places or alone, so that despite the activation of the protective device 1, there is no help for the person 8 having the accident. The same applies if the protective device 1 fails for whatever reasons, i.e., the protective device 1 responds, but the voltage cannot be switched off.

Figure 5:
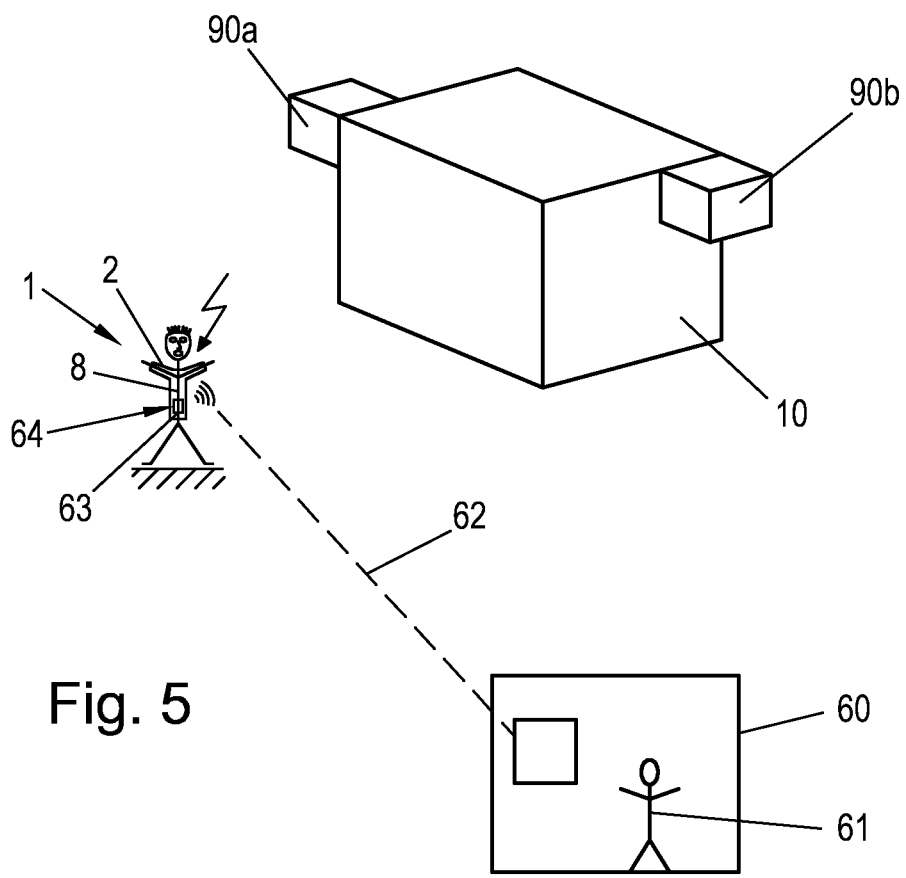
FIG. 5 shows an exemplary embodiment of the method according to the invention for notifying a remote location of an electrical accident involving a person wearing a protective device.

It can likewise be provided that a protective device 1 does not only generate an emergency signal S but establishes a radio link 62 (indicated by the dashed line) with a transmitter unit 64, such as a mobile radio transmitter 63, to a configured remote location 60 so that help for the person 8 having the accident is initiated or coordinated, preferably by a further person 61 at the remote location 60, as shown in FIG. 5. "Remote" means in this context that this further person 61 is at least so far away from the person 8 having the accident that this further person 61 can neither visually nor acoustically directly determine the condition of the accident victim. However, the second radio terminal 91 on the protective device 1 can of course also be used as the transmitter unit 64 if the range is sufficient. The further person 61 can, for example, be in an emergency center, which can be in a completely different location. The protective device 1 can establish the radio link 62 directly via the transmitter unit 64, for example by means of a mobile radio transmitter 63 which is integrated in the item of clothing 2, for example again as part of intelligent clothing.

Figure 6:
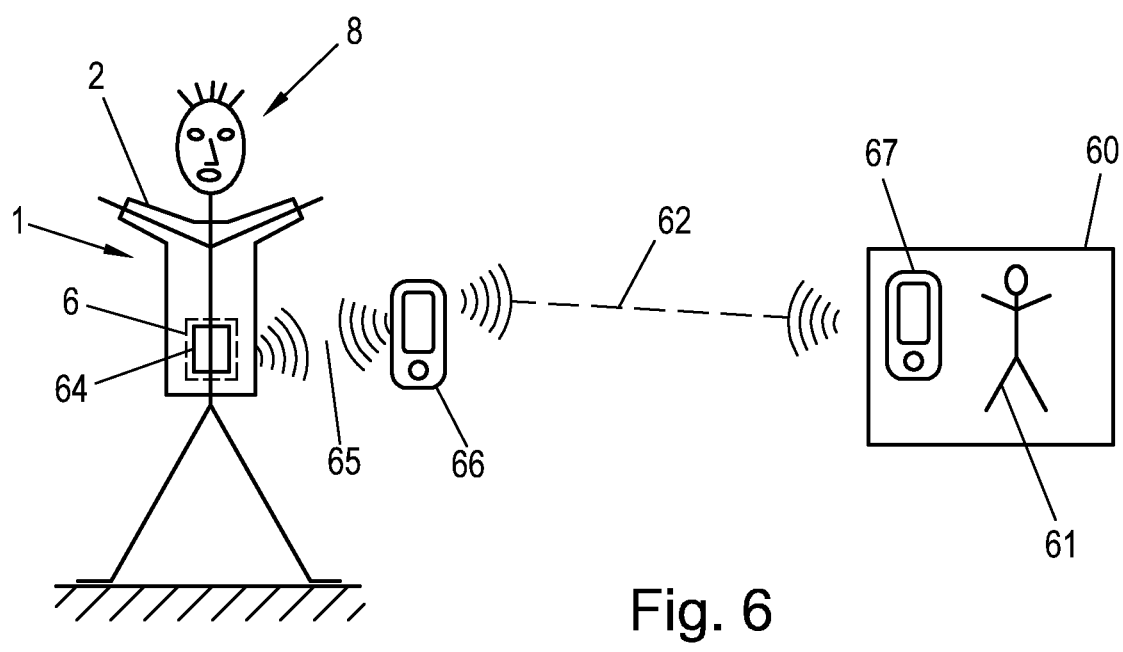
FIG. 6 shows the use of a mobile terminal for establishing the radio link to the remote location.

Alternatively, the protective device 1 can also establish the radio link 62 indirectly, for example, in that the protective device 1 connects, via the transmitter unit 64 and a suitable data connection 65, for example Bluetooth, to a mobile terminal 66, for example a smartphone (e.g., using Bluetooth), of the person 8, which then sets up the radio link 62 to the remote location 60, as shown in FIG. 6. A specific message can be sent via the radio link 62, for example a text message (SMS), a data transmission (for example, by e-mail) or a call can be made. The further person 61 in the remote location 60 can also carry a mobile terminal 67 with him, which can be connected to the radio link 62 if necessary, for example via a mobile radio network. It is obvious that the remote location 60 (e.g., the emergency center) does not have to be stationary, in particular, if the further person 61 also uses a mobile terminal 67 to be contacted.

The transmitting unit 64, for example in the form of a mobile radio transmitter 63, is preferably integrated in the evaluation unit 6 or also in the item of clothing 2 itself (for example, in the form of intelligent clothing). The transmitting unit 64 can be controlled by the evaluation unit 6 of the protective device 1.

The further person 61 can then coordinate help for the person 8 having the accident. An emergency center may, for example, be aware of the location of persons 8 who work on electrical systems 10 that are live or under voltage. For example, maintenance work is planned on a power grid as an electrical system 10 (as in FIG. 5), and it is known when and where this will be carried out. The protective device 1 can be assigned to a specific person 8 and can also have a unique identifier (for example, a mobile phone number). This way, an emergency call (also as a text message or an e-mail) coming into the emergency center from a protective device 1 can be assigned to a location and/or a person 8 so that the further person 61 can be specifically coordinated help by an emergency helper.

The protective device 1 can also be equipped with a positioning unit 72. For this purpose, for example, the positioning unit 72 such as a GPS (Global Positioning System) sensor can be arranged on the item of clothing 2 (as indicated by dashed lines in FIG. 7) or integrated in the item of clothing, for example intelligent clothing with integrated electronics. Other satellite navigation systems such as GALILEO can also be used, of course. However, there are naturally other ways of determining the position of a person 8 by means of a positioning unit 72. A conclusion about the current position could be drawn, for example, from the availability of WLAN (Wireless LAN) networks. A position could also be determined via a mobile radio network, for example, by means of GSM positioning.

Figure 7:
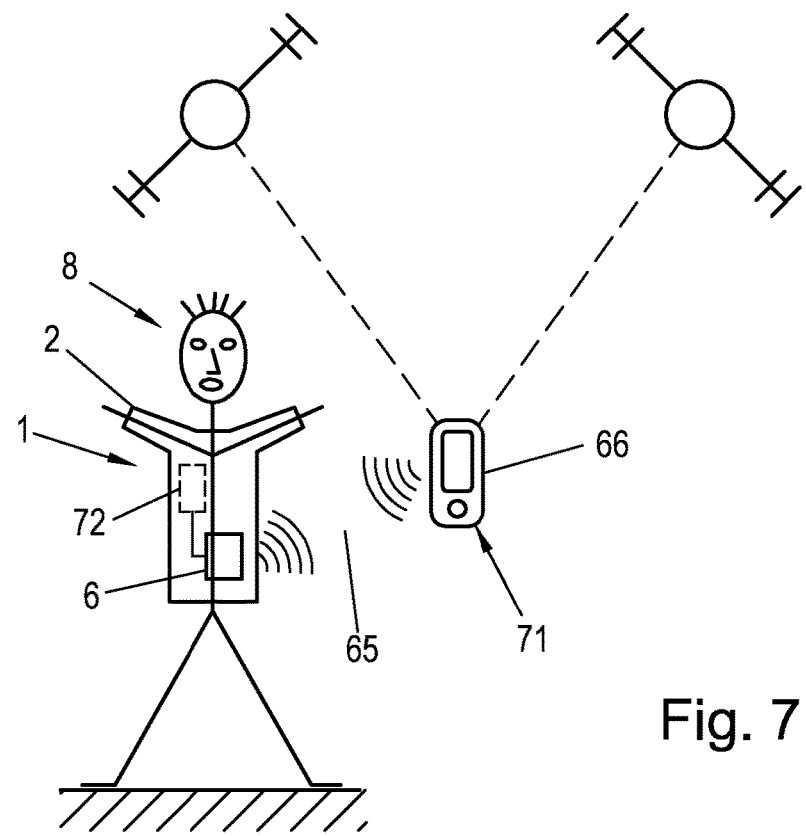
FIG. 7 shows the additional detection of the position of the person.

The protective device 1 can, however, also be connected to an external unit 71, which can carry out a position determination, as a positioning unit 72, as shown, for example, in FIG. 7. Today's mobile telephones or smart phones generally have a positioning system integrated in them so that a mobile terminal 66 can be used particularly advantageously as an external unit 71 for this purpose (as seen in FIG. 7). However, the external unit 71 can be a GPS receiver as well. The protective device 1 can thus be connected to the external unit 71 via a suitable data link 65, for example Bluetooth, in order to receive the current position of the person 8 from the external unit 71. To establish the link, a transmitting unit 64 could again be provided in the protective device 1, for example.

The current position can be stored in the protective device 1, preferably in the evaluation unit 6 of the protective device 1, preferably with further details about an electrical accident such as the date, time, duration of the body current or the level of the current flow, in order to allow for a later evaluation. The current position is understood to refer both to geographic coordinates and a specific location. Since many external units 71 often also have a positioning function, the location can also be used directly as the current position.

Of course, the current position or the current location can also be transmitted to the remote location 60 (as in FIG. 5 or 6) in order to assist with the coordination of assistance for the person 8 having the accident. The current position or the current location could also be transmitted to the remote location 60 at certain time intervals in order to always know a current position or a current location of the person 8.

Independently of the other functions of the protective device, the position or the location of the person 8 can be recorded and stored in the protective device 1, for example in order to generate a documentation of electrical accidents or for statistical records or evaluations of electrical accidents. In addition, further details such as date, time, duration of power contact, etc. can be stored.

It is obvious that when a remote location 60 is notified by the protective device 1 in the event of an electrical accident, additional information, for example data from further sensors 9 on the protective device 1, can also be transmitted about the condition of the person 8, for example the physical position of the person 8 (fall, person is lying down), pulse, ECG, respiration. Such additional information can be important for coordinating the help and rescue operations.

The remote location 60 can, of course, also be automated to the extent that, in the event of an incoming message of an electrical accident of a person 8, certain actions are automatically taken, for example the notification of an ambulance service or helper, possibly also with the specific position or location of person 8, possibly also with other existing data. In this case, the further person 61 would not be absolutely necessary.

To this end, the remote location 60 could also determine the location of one or more helper in the vicinity of the person 8 having the accident and specifically inform him about the electrical accident. The helper who is locally closest to the person 8 having the accident is preferably determined. For this purpose, the helper can be equipped with a communication unit, for example a mobile phone or smart phone, which is contacted by the remote location 60 or by the further person 61 at the remote location 60 with a corresponding message. The message could be a text message, email, or the like, or a phone call.

A helper in the vicinity of the person having the accident could be determined in that the locations of all possible helpers are known at the remote location 60. The current location could be continuously transmitted to the remote location 60, for example, via the communication units of the EMT helpers at predetermined intervals. However, a proximity could also be determined in such a way that it is determined whether a communication unit of the person 8 having the accident, for example a mobile terminal 66, can exchange messages with a communication unit of a helper, for example via Bluetooth, or whether both can receive the same WLAN network. This could also be continuously communicated to the remote location 60 by the respective communication unit so that the remote location 60 always has a current status.

Situations are conceivable in which a (switching) operation is carried out on the electrical system 10 by the emergency signal S, but this does not lead to the desired success, i.e., the absence of voltage on the part contacted. This can happen, for example, if an emergency electric circuit is interrupted but another electric circuit is available that is not connected to the emergency stop. It can therefore also be monitored in the electrical system 10 whether the switching action leads to the desired success within a predetermined time period, for example 100 ms. It can be determined, for example, whether the protective device 1 no longer receives an emergency signal S after the switching action. If the absence of voltage cannot be determined in the specified time period, a further (switching) action can be triggered in the electrical system 10, for example, in order to switch off at least one further electric circuit. It is often the case, for example, that only certain sockets or power supplies are connected to an emergency electric circuit while other electrical parts are in a different electric circuit. In this way, the emergency electric circuit could first be disconnected as described, and in a second step, if the first step was unsuccessful, a defined additional electric circuit could be disconnected. Of course, different hierarchies of electric circuits can be defined, which are switched off one after the other. An emergency electric circuit could be switched off first, for example, then an adjacent emergency electric circuit or an electric circuit for normal sockets, then an electric circuit for the IT infrastructure in a certain part of a building, then the whole building and finally the power supply for a server room.

It is also conceivable for several people to be in the work area at the same time in order to carry out work on current-carrying parts. In such situations, however, it can happen that an electrical accident involving a person 8 is not noticed by other persons in the vicinity, not even those in the immediate vicinity. This can also put other people at risk, for example, because they touch the person 8 who has become part of the electric circuit or because they also touch the live part. Apart from this, an efficient action to rescue the person 8 having the accident or to protect other people in the vicinity, for example by switching off or short-circuiting the electrical circuit or also by pushing the person 8 having the accident away, is only possible if at least one further person in the vicinity becomes aware of the electrical accident. In such cases, a protective device 1 according to the invention can also advantageously be used, as described by way of example with reference to FIG. 8.

Figure 8:
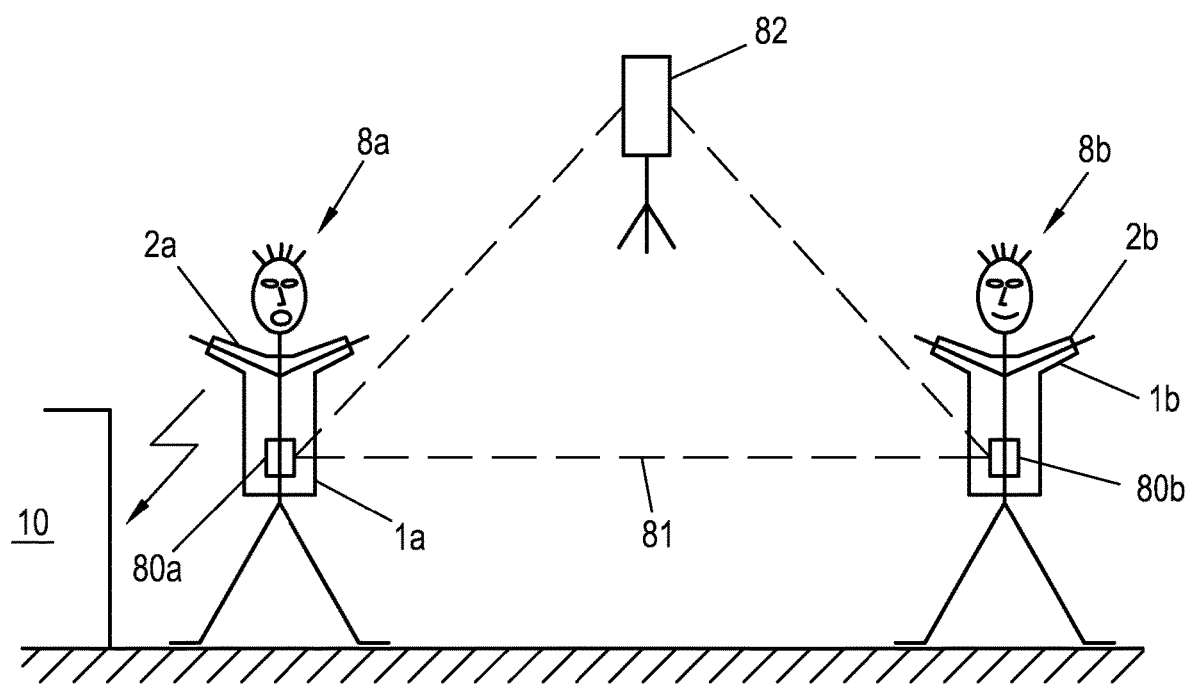
FIG. 8 shows a possible communication link between two protective devices.

It is assumed that a plurality of people 8a, 8b, each with a protective device 1a, 1b, are in the vicinity of a live component and that the protective devices 1a, 1b are in communication. For this purpose, each protective device 1a, 1b can be provided with a communication unit 80a, 80b in order to be able to set up a communication link 81, for example via Bluetooth. The communication link 81 can, however, also be established indirectly, for example, as explained in connection with FIG. 6, via a mobile terminal 66 of a person 8a, 8b. The communication units 80a, 80b of the two protective devices 1a, 1b do not have to communicate directly with one another. It would be conceivable, for example, for a communication center 82 to be set up in the work area with which the individual protective devices 1a, 1b are connected via their communication units 80a, 80b, as indicated in FIG. 8. In that case, the communication link 81 is established via the communication center 82. The communication link 81 can be set up permanently or set up also on an event-related basis. If a protective device 1a of a person 8a triggers an emergency signal S, because this person 8a becomes part of an electric circuit, the communication unit 80a of the protective device 1a informs the at least one further person 8b in the vicinity via the communication link 81 and the communication unit 80b of the protective device 1b. For this purpose, a corresponding signaling unit, for example an acoustic, visual or palpable alarm, can also be provided on a protective device 1. If a protective device 1 is additionally provided with a unique identifier, it is possible to also transmit which protective device 1 is affected in order to be able to locate the person 8a having the accident more easily. The help for a person 8a having the accident can thus be considerably accelerated.

Instead of setting up a communication center 82 in the work area, the communication described could also take place via a remote location 60 (at any distance away) as a communication center, for example as described in FIG. 5 or 6.

The protective device 1 of the person 8 having the accident, or a communication unit 80 of the protective device 1 or an external device 71 coupled to the protective device, for example a mobile phone that the person 8 is carrying, can also make further persons in the surrounding area, who may not be trained or have any special equipment, aware of the danger and the help that is needed with a loud acoustic signal, optionally also with spoken warning text. An acoustic warning such as "Warning—electrical accident—this person is under voltage. Do not touch this person. Interrupt the circuit or remove the person from the circuit" or "Warning—electrical accident—this person has suffered an electric shock. Touchable parts under voltage are nearby" would be conceivable, for example.

It is, of course, also possible to check, either continuously or at least at the beginning of the work, whether a radio link exists at all between the protective device 1 and the emergency signal input 21. If not, a corresponding alarm can be issued by the protective device 1, for example acoustically, visually or palpably. The same naturally applies if a low state of charge of an energy supply for the protective device 1 is detected in the protective device 1.

The invention claimed is:

1. Arrangement for carrying out work on an electrical system by a person, the arrangement comprising:
    a protective device including a second radio terminal and a transmitter unit, the protective device configured and arranged to
        be worn by the person,
        detect an electrical body current, and
        in the event that an unacceptable body current is detected, output an emergency signal via the second radio terminal and a first radio link and establish a second radio link between the transmitter unit and a remote location;
    an emergency signal input configured and arranged to receive the external emergency signal sent via the first radio link and the electrical system being configured and arranged to trigger a preset action when the emergency signal is received;
    a plurality of first radio terminals communicatively coupled to the electrical system, each of the plurality of first radio terminals are configured and arranged to establish the first radio link with the second radio terminal for receiving the emergency signal via the emergency signal input, and
    wherein the first radio link for sending the emergency signal is established between one of the first plurality of radio terminals and the second radio terminal.

2. The arrangement according to claim 1, characterized in that all of the plurality of first radio terminals are configured and arranged to use the same radio channel.

3. The arrangement according to claim 1, characterized in that the plurality of first radio terminals are configured and arranged to use different radio channels.

4. The arrangement according to claim 3, characterized in that the radio channel with the best signal quality is selectable for receiving the emergency signal.

5. The arrangement according to claim 1, characterized in that the protective device further includes
    an item of clothing having at least one sensor configured and arranged for detecting the body current, and wherein the item of clothing is configured and arranged to be worn by the person; and
    an evaluation unit configured and arranged to evaluate a signal detected by the at least one sensor and trigger the transmitter unit and the second radio terminal to emit the emergency signal in the event of a detected unacceptable body current.

6. The arrangement according to claim 5, characterized in that the protective device further includes at least one further sensor configured and arranged to detect a further state of the person wearing the protective device and/or a unit configured and arranged for determining the position or location of the person.

7. The arrangement according to claim 5, wherein the remote location is configured and arranged to be informed by the protective device in the event of an electrical accident.

8. The arrangement according to claim 7, characterized in that the protective device is also configured and arranged to transmit data from the at least one further sensor and/or the position or location of the person to the remote location.

9. The arrangement according to claim 7, characterized in that the remote location is further configured and arranged to coordinate assistance for the person after an electrical accident.

10. The arrangement according to claim 1, further including a second protective device configured and arranged to be worn by at least one further person in the area where the person is working,
    wherein the protective device of the person and the second protective device of the at least one further person are configured and arranged to establish a communication link, and
    wherein the protective device of the person is further configured and arranged to inform the second protective device about an electrical accident of the person via the communication link.

11. The arrangement according to claim 10, characterized in that the protective devices each comprise a communication unit configured and arranged for establishing the communication link.

12. The arrangement according to claim 11, further including a communication center communicatively connected to the communication units and configured and arranged to establish the communication link.

13. The arrangement, according to claim 1, wherein the protective device is further configured and arranged to output an acoustic warning and/or an acoustic warning text in the event of an electrical accident.

14. The arrangement according to claim 1, wherein the protective device is further configured and arranged to output an alarm in the event that there is no radio link.

15. The arrangement according to claim 1, characterized in that the emergency signal input or the protective device is configured and arranged to
    check, after a predetermined time period, whether the emergency signal is still present, and
    trigger at least one further preset action in the electrical system if the emergency signal is still present after said predetermined time period.

16. The arrangement according to claim 1, wherein the transmitter unit is a mobile radio transmitter.

17. The arrangement according to claim 1, wherein the transmitter unit is further configured and arranged to establish the second radio link via a mobile terminal that is in data connection with the transmitter unit.

18. Method for carrying out work on an electrical system by a person, the method including the following steps:
    the person wears a protective device for detecting an electrical body current, the protective device including a second radio terminal and a transmitter unit, establishing a first radio link between the second radio terminal of the protective device and an emergency signal input of the electrical system, establishing a second radio link between the transmitter unit and a remote location, in the event that an unacceptable body current is detected by the protective device, an emergency signal is output via the first radio link and the second radio link, receiving the emergency signal at the emergency signal input of the electrical system via the first radio link, in response to the reception of the emergency signal, triggering a preset action in the electrical system, wherein the first radio link is established between one of a plurality of first radio terminals communicatively coupled to the electrical system and the second radio terminal of the protective device.

19. The method according to claim 18, further including the step of the protective device informing the remote location in the event of an electrical accident.

20. The method according to claim 19, further including the step of transmitting to the remote location data from at least one further sensor on the protective device and/or the position or location of the person via the protective device.

21. The method according to claim 19, further including the step of coordinating help for the person after an electrical accident by the remote location.

22. The method according to claim 18, further including the steps of at least one further person wearing another protective device positioned in the area where the person is working, establishing a communication link between the protective device of the person and the other protective device of the at least one further person, the protective device of the person informs the other protective device of the at least one further person about an electrical accident of the person via the communication link.

23. The method according to claim 18, further including the step of the protective device outputting an acoustic warning and/or an acoustic warning text in the event of an electrical accident.

24. The method according to claim 18, further including the step of the protective device outputting an alarm in the event that there is no radio link.

25. The method according to claim 18, further including the steps of the emergency signal input or the protective device checking after a predetermined time period whether the emergency signal is still present, and triggering at least one further preset action by the electrical system if the emergency signal is still present after said time period.

* * * * *